(12) United States Patent
Lian et al.

(10) Patent No.: US 7,583,996 B2
(45) Date of Patent: Sep. 1, 2009

(54) ATRIAL OVERDRIVE PACING IN NON-ATRIAL TRACKING MODE WHILE MAINTAINING AV SYNCHRONY

(75) Inventors: Jie Lian, Beaverton, OR (US); Christopher S. de Voir, Tigard, OR (US); Garth Garner, Tigard, OR (US); Hannes Kraetschmer, West Linn, OR (US); Dirk Müssig, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 93 days.

(21) Appl. No.: 11/560,099

(22) Filed: Nov. 15, 2006

(65) Prior Publication Data

US 2008/0114409 A1     May 15, 2008

(51) Int. Cl.
*A61N 1/368* (2006.01)
(52) U.S. Cl. ......................................... 607/14
(58) Field of Classification Search ............... 607/9, 607/14
See application file for complete search history.

(56) References Cited

U.S. PATENT DOCUMENTS

| | | | | |
|---|---|---|---|---|
| 4,920,965 A | * | 5/1990 | Funke et al. | 607/9 |
| 5,247,929 A | * | 9/1993 | Stoop et al. | 607/14 |
| 5,534,017 A | * | 7/1996 | van Krieken et al. | 607/14 |
| 5,931,856 A | * | 8/1999 | Bouhour et al. | 607/9 |
| 6,311,088 B1 | * | 10/2001 | Betzold et al. | 607/14 |
| 6,606,517 B1 | * | 8/2003 | Park et al. | 607/14 |
| 7,308,306 B1 | * | 12/2007 | Park et al. | 607/9 |
| 2003/0078627 A1 | * | 4/2003 | Casavant et al. | 607/9 |
| 2005/0187585 A1 | * | 8/2005 | Mussig et al. | 607/9 |
| 2007/0299475 A1 | * | 12/2007 | Levin et al. | 607/9 |

\* cited by examiner

*Primary Examiner*—George R Evanisko
*Assistant Examiner*—Amanda Patton
(74) *Attorney, Agent, or Firm*—Dalina Law Group, P.C.

(57) ABSTRACT

Heart stimulator that stimulates at least a heart's right atrium and ventricle in an atrium asynchronous stimulation mode with an overdrive stimulation rate. Interposes one resynchronization cycle after a sensed atrial event to regain AV synchrony during otherwise asynchronous stimulation mode. Allows for pacing mode that can pace the atrium with an overdrive stimulation rate in dual-chamber asynchronous mode while maintaining the AV synchrony and is called DDI (R)+. In DDI(R)+, pacemaker performs an atrial asynchronous (V synchronous) pacing mode such as DDI or DDI(R). The overdrive stimulation rate (OSR) is either a fixed rate (programmed by the external device) that is thought to be above the underlying intrinsic atrial rate, or is dynamically adjusted according to the measured atrial cycle length to be slightly above intrinsic atrial rate. The overdrive stimulation rate may be based on an intrinsic atrial rate or on hemodynamic need. DDI(R)+ timing may be ventricle-based.

8 Claims, 10 Drawing Sheets

ATRIAL OVERDRIVE PACING IN NON-ATRIAL TRACKING MODE WHILE MAINTAINING AV SYNCHRONY

BACKGROUND OF THE INVENTION

1. Field of the Invention

The invention refers to a heart stimulator for stimulating at least one atrium and one ventricle of a heart by means of electrical stimulation pulses in an overdrive mode of pacing wherein the atrium and the ventricle are stimulated with an overdrive stimulation rate that is thought to be higher than an intrinsic heart rate. More particular, the invention is directed to dual-chamber (RA-RV), three-chamber (BiA-RV, or RA-BiV), or four-chamber (BiA-BiV) implantable cardiac devices including pacemakers, defibrillators and cardioverters, which stimulate cardiac tissue electrically to control the patient's heart rhythm.

2. Description of the Related Art

Implantable heart stimulators can be used for treating a variety of heart disorders like bradycardia, tachycardia or fibrillation.

Depending on the disorder to be treated, such heart stimulator generates electrical stimulation pulses that are delivered to the heart tissue (myocardium) of a respective heart chamber according to an adequate timing regime. Delivery of stimulation pulses to the myocardium is usually achieved by means of an electrode lead that is electrically connected to a stimulation pulse generator inside a heart stimulator's housing and that carries a stimulation electrode in the region of it's distal end. A stimulation pulse having strong enough strength causes an excitation of the myocardium that in turn is followed by a contraction of the respective heart chamber. A stimulation pulse also is called a pace. Similarly, pacing a heart chamber means stimulating a heart chamber by delivery of a stimulation pulse (pace).

In order to be able to sense a contraction a heart chamber that naturally occurs without artificial stimulation and that is called intrinsic, the heart stimulator usually comprises at least one sensing stage that is connected to a sensing electrode on said electrode placed in the heart chamber. An intrinsic excitation of a heart chamber results in characteristic electrical potentials that can be picked up via the sensing electrode and that can be evaluated by the sensing stage in order to determine whether an intrinsic excitation—called: intrinsic event—has occurred.

Usually, a heart stimulator features separate stimulation generators for each heart chamber to be stimulated. Therefore, in a dual chamber pacemaker, usually an atrial and a ventricular stimulation pulse generator for generating atrial and ventricular stimulation pulses are provided. Delivery of an atrial or a ventricular stimulation pulse causing an artificial excitation of the atrium or the ventricle, respectively, is called an atrial stimulation event AP (atrial paced event) or a ventricular stimulation event VP (ventricular paced event), respectively.

Similarly, common heart stimulators feature separate sensing stages for each heart chamber to be of interest. In a dual chamber pacemaker usually two separate sensing stages, an atrial sensing stage and a ventricular sensing stage, are provided that are capable to detect intrinsic atrial events AS (atrial sensed event) or intrinsic ventricular events VS (ventricular sensed event), respectively.

By means of a sensing stage for a heart chamber to be stimulated, the pacemaker is able to only trigger stimulation pulses when needed that is when no intrinsic excitation of the heart chamber occurs in time. Such mode of pacing a heart chamber is called demand mode. In the demand mode the pacemaker schedules an atrial or a ventricular escape interval that causes triggering of an atrial or ventricular stimulation pulse when the escape interval times out. Otherwise, if an intrinsic atrial or ventricular event is detected prior to time out of the respective atrial or ventricular escape interval, triggering of the atrial or ventricular stimulation pulse is inhibited.

Depending upon which chambers of heart are stimulated and which sense events are used different modes of stimulation become available. These modes of stimulation are commonly identified by a three letter code wherein the first letter identifies the chamber or chambers to be stimulated such as V for a ventricle to be stimulated, A for an atrium to be stimulated and D (dual) for both, ventricle and atrium to be stimulated. Similarly, the second letter characterizes the chamber or chambers sensed events may origin from (V: ventricle, A: atrium, D: ventricle and atrium). The third letter characterizes the mode of delivery of stimulation pulses: T=triggered, I=inhibited and D=dual (T+I). A fourth letter "R" may characterize a rate adaptive heart stimulator that comprises an activity sensor or some other means for determining the hemodynamic need of a patient in order to adapt the stimulation rate accordingly.

A dual chamber pacemaker featuring an atrial and a ventricular sensing stage and an atrial and a ventricular stimulation pulse generator can be operated in a number of stimulation modes like VVI, wherein atrial sense events are ignored and no atrial stimulation pulses are generated, but only ventricular stimulation pulses are delivered in a demand mode, AAI, wherein ventricular sense events are ignored and no ventricular stimulation pulses are generated, but only atrial stimulation pulses are delivered in a demand mode, or DDD, wherein both, atrial and ventricular stimulation pulses are delivered in a demand mode. In such DDD mode of pacing, ventricular stimulation pulses can be generated in synchrony with sensed intrinsic atrial events and thus in synchrony with an intrinsic atrial rate, wherein a ventricular stimulation pulse is scheduled to follow an intrinsic atrial contraction after an appropriate atrioventricular delay (AV-delay; AVD), thereby maintaining the hemodynamic benefit of atrioventricular synchrony.

In some cases, a DDI mode of stimulation may be adequate. In such DDI mode, a ventricular stimulation pulse is not synchronized with a preceding atrial sense event (not "triggered" by an atrial sense event). However, both, atrium and ventricle, are stimulated in a demand mode wherein stimulation pulses are inhibited if an intrinsic event is sensed prior to time out of a respective escape interval.

In particular if an overdrive stimulation is needed, DDI mode pacing may be adequate. When stimulating a heart with an overdrive stimulation rate it is attempted to deliver a (premature) stimulation pulse prior to a possible intrinsic excitation and thus render a respective heart chamber refractory so that it is not susceptible to any further (natural) excitation during a (natural) refractory period needed by the cells of the myocardium to repolarize and thus become susceptible to further excitation again.

Atrial overdrive pacing is useful in a number of applications.

One typical application is to prevent atrial fibrillation (AF). Possible mechanisms by which atrial pacing may be effective include suppression of premature supraventricular beats, elimination of delayed atrial conduction, and atrial pauses that may trigger or facilitate reentry circuits favoring the initiation of AF. Various algorithms have been developed, including dynamic (permanent) atrial overdrive pacing, post- AES (temporary) atrial rate stabilization, post-mode-switch (temporary) overdrive pacing, etc.

Another application is for atrial capture verification during atrial pacing threshold measurement. For patients with intact AV node, the presence of a conducted ventricular sense (Vs) after a premature atrial stimulation pulse (Ap) indicates that the atrial stimulation pulse was strong enough to be effective and thus to cause "capture" of the atrium whereas the absence of a ventricular sense event Vs after the atrial stimulation pulse Ap indicates atrial non-capture. For patient without intact AV node, the atrial non-capture can be suspected on the detection of intrinsic atrial sense (As) after the atrial stimulation pulse Ap since the atrial stimulation pulse was unable to render the atrial myocardium refractory and thus to suppress intrinsic atrial excitation. For both scenarios, atrial overdrive pacing above the intrinsic atrial rate is required.

In a dual-chamber device, atrial overdrive pacing can be achieved in both DDD(R) mode and DDI(R) mode. The DDD(R) mode is useful to maintain the AV synchrony during atrial overdrive pacing, but has intrinsic risk of pacemaker-mediated tachycardia (PMT). On the other hand, the DDI(R) mode is free of PMT but may also lose the hemodynamic benefit of AV synchrony.

Therefore, there is a need to implement the atrial overdrive pacing in DDI(R) mode (thus eliminate the risk of PMT) while still maintaining the AV synchrony (thus enjoy the associated hemodynamic benefits).

For the purpose of this disclosure, the following abbreviations are used:

TABLE 1

| Abbreviation | Meaning |
| --- | --- |
| AES | Atrial extrasystole |
| Ap | Atrial pace event |
| As | Atrial sense event |
| Ars | Atrial refractory sense |
| A | Any atrial event |
| AsVI | The interval measured from the As to the following Vp or Vs |
| AUI | Atrial upper interval |
| AVD | AV delay as applied by the pacemaker (in contrast to intrinsic AV delay) |
| FFPW | Far field protection window after Vs or Vp |
| MS | Mode switch |
| ODI | Overdrive pacing interval (s): ODI = 60/OSR |
| OSR | Overdrive stimulation rate (ppm): OSR = 60/ODI |
| PMT | Pacemaker mediated tachycardia |
| PVAB | Post-ventricular atrial blanking period |
| PVARP | Post-ventricular atrial refractory period |
| Re-Sync | Re-synchronization pacing cycle in DDI(R)+ mode |
| SW | Safety window |
| URL | Upper rate limit |
| VAI | VA interval (duration of the VA timer) |
| VES | Ventricular extra-systole |
| Vp | Ventricular pace |
| Vs | Ventricular sense |
| V | Any ventricular event |
| VT | Ventricular tachycardia |

BRIEF SUMMARY OF THE INVENTION

According to the present invention the object of the invention is achieved by a heart stimulator featuring:

at least one sensing stage connected or being connectable to an electrode lead comprising an electrode for picking up electric potentials inside at least one atrium and one ventricle of a heart, said sensing stage being adapted to sense an excitation or a contraction of a heart chamber, at least one stimulation pulse generator adapted to generate electric stimulation pulses and being connected or being connectable to an electrode lead comprising a stimulation electrode for delivering electric stimulation pulses to at least said atrium and said ventricle of the heart, and a control unit that is connected to said sensing stage and to said stimulation pulse generator.

The control unit is adapted:

to trigger stimulation pulses that are generated by the stimulation pulse generator and that are to be delivered via said electrode lead, to perform at least a DDI mode of pacing, wherein atrial and ventricular stimulation pulses are triggered in an atrium asynchronous manner when a respective atrial or ventricular escape interval times out because no intrinsic atrial or ventricular contraction is sensed during said atrial or ventricular escape interval, respectively, wherein triggering of an atrial or a ventricular stimulation pulse is inhibited, when an intrinsic atrial or ventricular contraction, respectively, is sensed prior to time out of the respective atrial or ventricular escape interval, and wherein the atrial and the ventricular escape interval correspond to an overdrive stimulation rate, that is thought to be higher than an intrinsic heart rate, and to resynchronize said ventricular escape interval and said atrial escape interval during said DDI mode of pacing with an intrinsic heart rhythm when an intrinsic atrial event AS is sensed prior to time out of an atrial escape interval.

Generally, the objective of the invention is solved by a heart stimulator that is adapted to stimulate at least a right atrium and a right ventricle of a heart in an atrium asynchronous stimulation mode with an overdrive stimulation rate, wherein the heart stimulator is further adapted to interpose one resynchronization cycle after a sensed atrial event in order to regain AV synchrony during the otherwise asynchronous stimulation mode.

The pacemaker according to the invention allows for a pacing mode that can pace the atrium with an overdrive stimulation rate in dual-chamber asynchronous mode while maintaining the AV synchrony. This mode is called DDI(R)+ mode for the purpose of present disclosure.

In DDI(R)+, the pacemaker performs an atrial asynchronous (V synchronous) pacing mode such as DDI or DDI(R). The overdrive stimulation rate (OSR) is either a fixed rate (programmed by the external device) that is thought to be above the underlying intrinsic atrial rate, or is dynamically adjusted according to the measured atrial cycle length so that it is slightly above the intrinsic atrial rate. Corresponding to the overdrive stimulation rate. ODI is an overdrive stimulation interval that determines the duration of one stimulated heart cycle and is reciprocal to the overdrive stimulation rate: ODI=60/OSR.

Preferably, the control unit is adapted to adjust the overdrive stimulation rate based on an intrinsic atrial rate sensed via the sensing stage such that the overdrive stimulation rate is higher than said sensed intrinsic atrial rate prior to performing the DDI mode of pacing with that overdrive rate.

Alternatively, the control unit may be adapted to adjust the overdrive stimulation rate based on an activity signal determined by means of an activity sensor such that the overdrive stimulation rate is higher than an adapted heart rate corresponding to a hemodynamic need that corresponds to the activity as determined by the activity sensor.

In a preferred embodiment, the timing cycle of DDI(R)+ is ventricle-based.

Accordingly it is preferred that the ventricular escape interval is a VV-interval started by a ventricular event, said VV-interval being reciprocal to the overdrive stimulation rate.

Similarly, it is preferred that the atrial escape interval is a VA-interval started by a ventricular event. The atrial escape interval preferably is a VA-interval that corresponds to: VAI=VV−AVD wherein AVD is a predetermined atrioventricular delay interval. The atrioventricular delay interval AVD preferably is adjustable.

In such pacemaker, like in a conventional DDI(R) mode, after each used ventricular event (Vs or Vp), a VV timer setting the ventricular escape interval is started with duration of ODI. The ventricular stimulation pulse Vp will be inhibited if there is a used (not ignored) ventricular sense event Vs prior to the timeout of the VV timer, otherwise a ventricular stimulation pulse Vp will be delivered at the timeout of the VV timer. The ventricular escape interval is the VV interval that equals the overdrive interval ODI. Meanwhile, after each used ventricular event (Vs or Vp), a VA timer defining the atrial escape interval is started with duration of VAI=ODI−AVD, where AVD is a programmed AV delay (or may be dynamically adjusted by other features). The atrial stimulation pulse Ap will be inhibited if there is a used atrial sense event As prior to the timeout of the VA timer, otherwise the atrial stimulation pulse Ap will be delivered at the timeout of the VA timer (with VA interval=ODI−AVD). Ideally, the ODI should be shorter than the intrinsic atrial cycle length to achieve overdrive pacing of the atrium. The ODI can be a programmed value, or can be dynamically adjusted according to the measured atrial rate or the sensor indicated rate, see above.

As long as atrium is continuously overdriven, the operation of DDI(R)+ is identical to conventional DDI(R).

The key difference is when an atrial stimulation pulse Ap is inhibited by a used As, that is, when the atrial overdrive is lost. After a used As, the device triggers a Re-Sync cycle and starts monitoring the following ventricular event (Vs or Vp). Upon detection of the following ventricular event, the Re-Sync cycle is implemented so that the following VV interval and VA interval are recalculated based on the just measured AV interval. By this means, the device tries to regain control of the atrial overdrive pacing. Alternatively, the Re-Sync cycle can also be triggered by an Ars detected during the late PVARP. The Re-Sync cycle will be implemented if the Ars is followed by a conducted ventricular sense event Vs within a predefined AV control time. Otherwise, the Re-Sync cycle will be discarded.

Accordingly, it is preferred, that the control unit is adapted to resynchronize said ventricular escape interval and said atrial escape interval by recalculating said ventricular escape interval and said atrial escape interval based on an ASV-Interval, which begins with said intrinsic atrial event AS that triggered resynchronization and which end with the following ventricular event V.

The Re-Sync cycle is re-triggerable. That is, after an Ars or As triggers a Re-Sync cycle, if there is another Ars or As before the detection of the ventricular event, the second Ars or As will re-trigger the Re-Sync cycle. By this means, upon detection of the following ventricular event, the latest Ars or As will be based upon to measure the AV interval, which is used for the re-calculation of the VV interval and the VA interval to implement the Re-Sync cycle.

Several additional features are added to handle special conditions, such as safety window (SW) Vs and Vp, atrial upper interval (AUI), upper rate limit (URL), ventricular extra-systole (VES), high atrial/ventricular rate detection, etc.

The details of the DDI(R)+ feature can be understood from the following drawings and the corresponding text descriptions.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
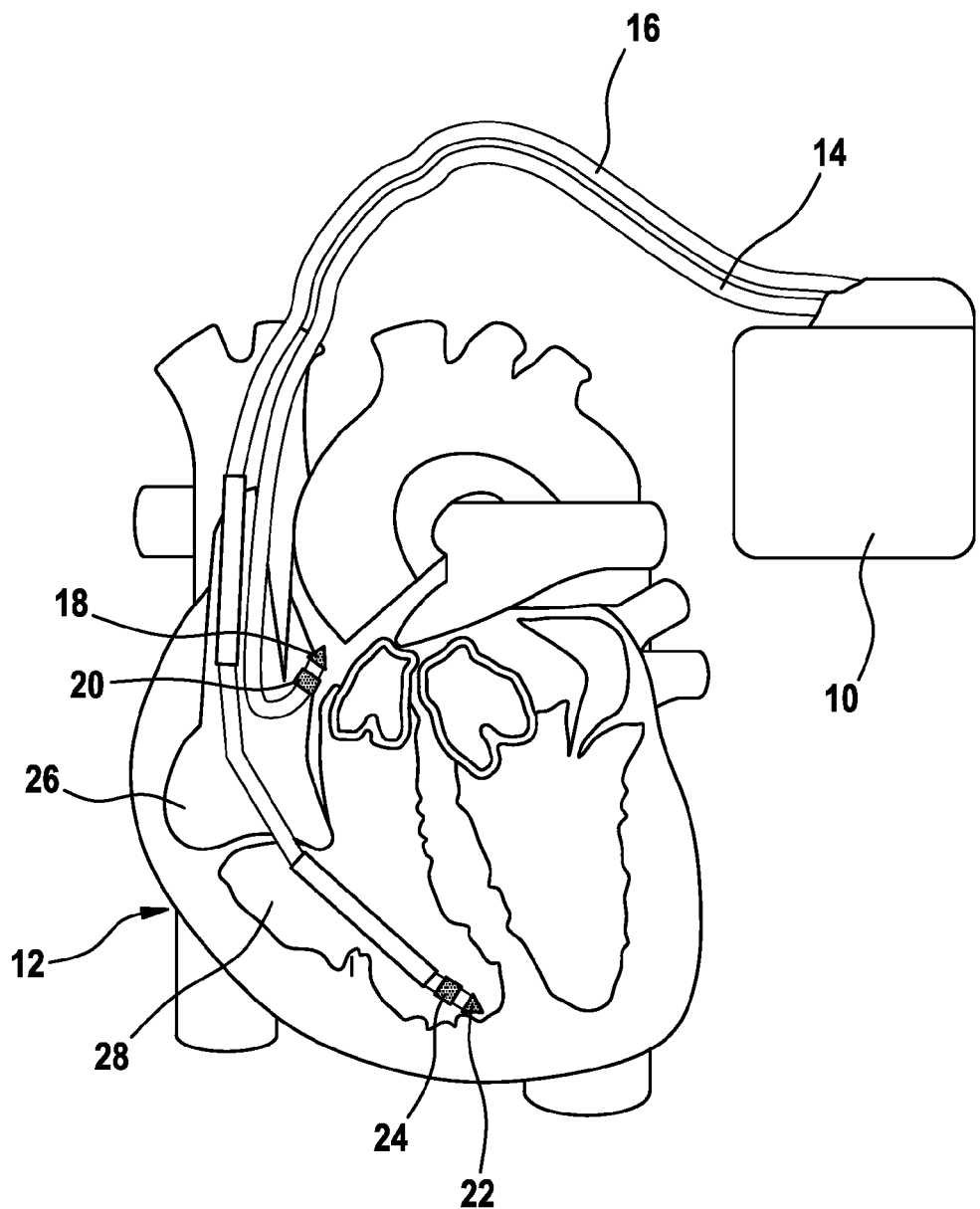
FIG. 1 shows a dual chamber pacemaker connected to leads placed in a heart.

In FIG. 1 a dual chamber pacemaker 10 as heart stimulator connected to pacing/sensing leads placed in a heart 12 is illustrated. The pacemaker 10 is electrically coupled to heart 12 by way of leads 14 and 16. Lead 14 has a pair of right atrial electrodes 18 and 20 that are in contact with the right atria 26 of the heart 12. Lead 16 has a pair of electrodes 22 and 24 that are in contact with the right ventricle 28 of heart 12. Electrodes 18 and 22 are tip-electrodes at the very distal end of leads 14 and 16, respectively. Electrode 18 is a right atrial tip electrode RA-Tip and electrode 22 is a right ventricular tip electrode 22. Electrodes 20 and 24 are ring electrodes in close proximity but electrically isolated from the respective tip electrodes 18 and 22. Electrode 20 forms a right atrial ring electrode RA-Ring and electrode 24 forms a right ventricular ring electrode RV-Ring.

Figure 2:
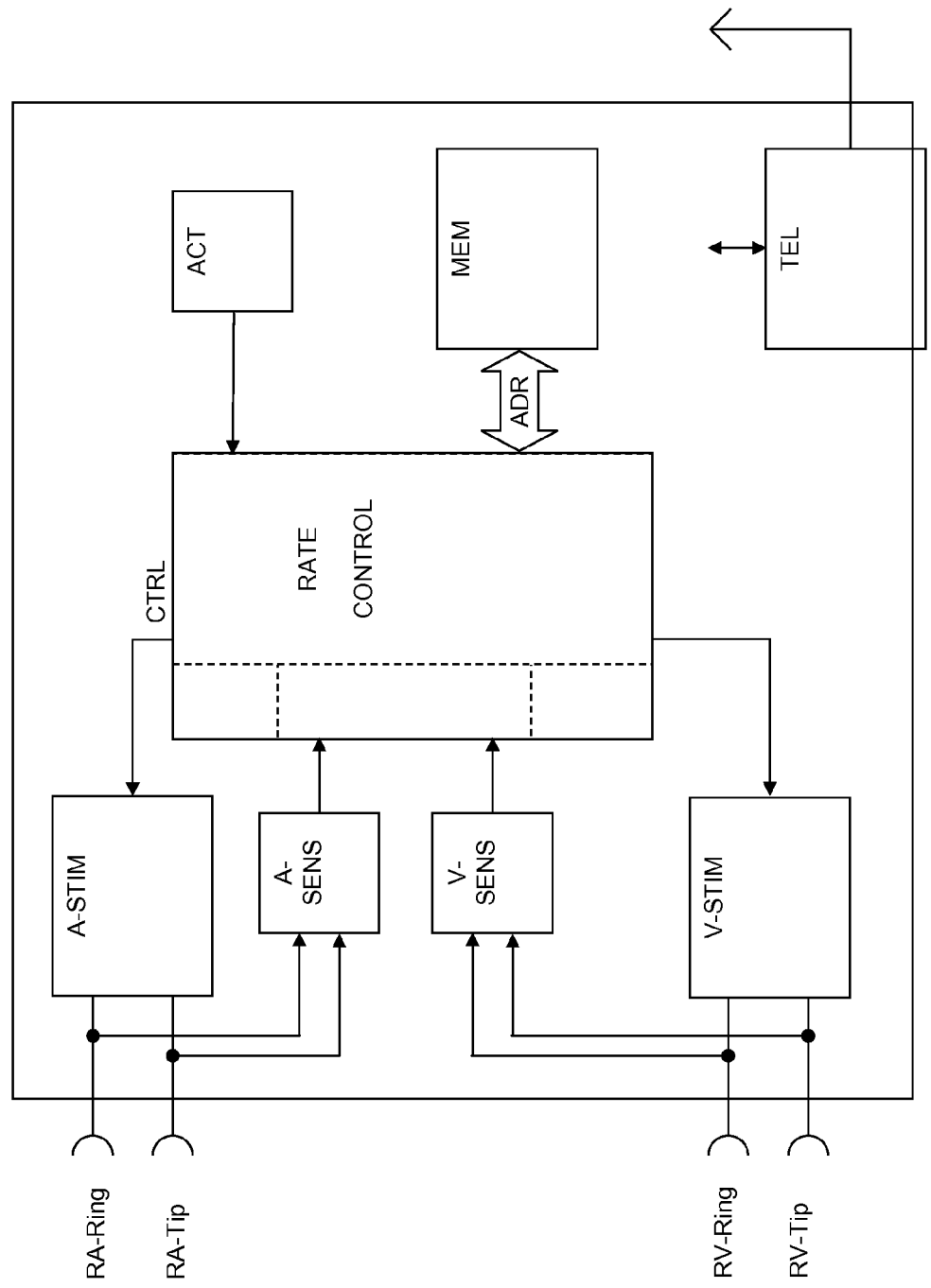
FIG. 2 is a block diagram of a heart stimulator according to the invention.

Referring to FIG. 2 a simplified block diagram of a dual chamber pacemaker 10 is illustrated. During operation of the pacemaker leads 14 and 16 are connected to respective output/input terminals of pacemaker 10 as indicated in FIG. 1 and carry stimulating pulses to the tip electrodes 18 and 22 from an atrial stimulation pulse generator A-STIM and a ventricular pulse generator V-STIM, respectively. Further, electrical signals from the atrium are carried from the electrode pair 18 and 20, through the lead 14, to the input terminal of an atrial channel sense amplifier A-SENSE; and electrical signals from the ventricles are carried from the electrode pair 22 and 24, through the lead 16, to the input terminal of a ventricular sense channel amplifier V-SENSE.

Controlling the dual chamber pacer 10 is a control unit CTRL that is connected to sense amplifiers A-SENSE and V-SENSE that form respective sensing stages and to stimulation pulse generators A-STIM and V-STIM. Control unit CTRL receives the output signals from the atrial sense amplifier A-SENSE and from the ventricular sense amplifier V-SENSE. The output signals of sense amplifiers A-SENSE and V-SENSE are generated each time that a P-wave representing an intrinsic atrial event or an R-wave representing an intrinsic ventricular event, respectively, is sensed within the heart 12. An As-signal is generated, when the atrial sense amplifier A-SENSE detects a P-wave and a Vs-signal is generated, when the ventricular sense amplifier V-SENSE detects an R-wave.

Control unit CTRL also generates trigger signals that are sent to the atrial stimulation pulse generator A-STIM and the ventricular stimulation pulse generator V-STIM, respectively. These trigger signals are generated each time that a stimulation pulse is to be generated by the respective pulse generator A-STIM or V-STIM. The atrial trigger signal is referred to simply as the "A-pulse", and the ventricular trigger signal is referred to as the "V-pulse". During the time that either an A-pulse or V-pulse is being delivered to the heart, the corresponding sense amplifier, A-SENSE and/or R-SENSE, is typically disabled by way of a blanking signal presented to these amplifiers from the control unit CTRL, respectively. This blanking action prevents the sense amplifiers A-SENSE and V-SENSE from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Furthermore, atrial sense events As recorded shortly after delivery of a V-pulses during a preset time interval called post ventricular atrial refractory period (PVARP) are generally recorded but ignored. Such atrial sense event during PVARP is marked Ars herein after.

Control unit CTRL comprises circuitry for timing ventricular and/or atrial stimulation pulses according to an adequate stimulation rate that can be adapted to a patient's hemodynamic need as pointed out below.

Still referring to FIG. 2, the pacer 10 may also include a memory circuit MEM that is coupled to the control unit CTRL over a suitable data/address bus ADR. This memory circuit MEM allows certain control parameters, used by the control unit CTRL in controlling the operation of the pacemaker 10, to be programmably stored and modified, as required, in order to customize the pacemaker's operation to suit the needs of a particular patient. Such data includes the basic timing intervals used during operation of the pacemaker. Further, data sensed during the operation of the pacer may be stored in the memory MEM for later retrieval and analysis.

A telemetry circuit TEL is further included in the pacemaker 10. This telemetry circuit TEL is connected to the control unit CTRL by way of a suitable command/data bus. Telemetry circuit TEL allows for wireless data exchange between the pacemaker 10 and some remote programming or analyzing device which can be part of a centralized service center serving multiple pacemakers.

The pacemaker 10 in FIG. 1 is referred to as a dual chamber pacemaker because it interfaces with both the right atrium 26 and the right ventricle 28 of the heart 12. Those portions of the pacemaker 10 that interface with the right atrium, e.g., the lead 14, the P-wave sense amplifier A-SENSE, the atrial stimulation pulse generator A-STIM and corresponding portions of the control unit CTRL, are commonly referred to as the atrial channel. Similarly, those portions of the pacemaker 10 that interface with the right ventricle 28, e.g., the lead 16, the R-wave sense amplifier V-SENSE, the ventricular stimulation pulse generator V-STIM, and corresponding portions of the control unit CTRL, are commonly referred to as the ventricular channel.

In order to allow rate adaptive pacing in a DDDR or a DDIR mode, the pacemaker 10 further includes a physiological sensor ACT that is connected to the control unit CTRL of the pacemaker 10. While this sensor ACT is illustrated in FIG. 2 as being included within the pacemaker 10, it is to be understood that the sensor may also be external to the pacemaker 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, pH of blood, body motion, and the like. The type of sensor used is not critical to the present invention. Any sensor capable of sensing some physiological parameter relatable to the rate at which the heart should be beating can be used. Such sensors are commonly used with "rate-responsive" pacemakers in order to adjust the rate of the pacemaker in a manner that tracks the physiological needs of the patient.

Now the operation of pacemaker 10 during the DDI(R)+ mode shall be illustrated.

The DDI(R)+ mode allows effective atrial overdrive pacing. The ventricle can be overdriven as well with short AVD (e.g., 70 ms or adaptively adjust to shorter than the measured intrinsic AV conduction time, or in the case of AV block). This allows simultaneous overdrive pacing in both atrium and ventricle. This is particularly useful for situations that prefer ventricular pacing such as for patients with hypertrophic obstructive cardiomyopathy, or in cardiac resynchronization therapy (CRT). On the other hand, conducted ventricular events (Vs) can be preserved by programming a long AVD (e.g., 250 ms or adaptively adjust to longer than the measured intrinsic AV conduction time that is the natural atrialventricular time delay). This is particularly useful to minimize right ventricular pacing, which has been demonstrated to be associated with hemodynamic deterioration and potential proarrhythmic effect. When programming a moderate AVD that is comparable to the intrinsic AV conduction time, both Vs and Vp may follow the atrial stimulation pulse Ap. The DDI(R)+ mode supports all above conditions.

In the following, we first consider the conditions that both atrium and ventricle are overdriven with a short AVD. Then we consider the conditions that atrium is overdriven while conducted Vs is encouraged by programming a long AVD. Condition that Vs and Vp are mixed with moderate AVD is also discussed.

Figure 3:
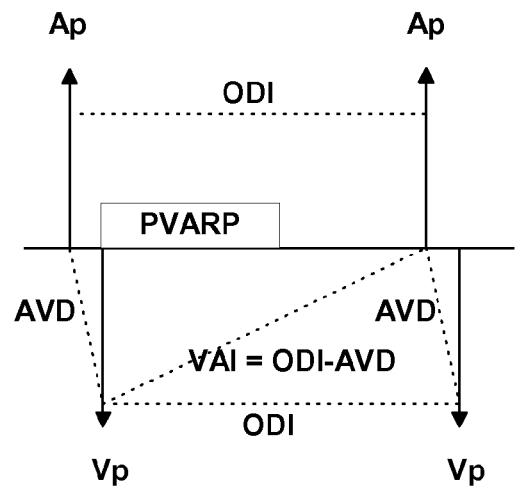
FIG. 3 is a diagram illustrating a typical cycle of DDI(R)+ where both atrium and ventricle are overdriven.

Refer to FIG. 3. Both atrium and ventricle are overdriven at a cycle length ODI with a short AVD. After each ventricular stimulation pulse Vp, a VV timer and a separate VA timer start. The VV timer times out after duration of the overdrive interval ODI after which another ventricular stimulation pulse Vp will be delivered. The VA timer times out after duration of VAI=ODI−AVD, after which another atrial stimulation pulse Ap will be delivered. As known in the art, the timing control is typical of the conventional DDI(R) mode. As known in the art, the PVARP after a ventricular stimulation pulse Vp can be a programmed value, or can be dynamically adjusted based on the measured heart rate. In a typical embodiment, the PVARP after ventricular stimulation pulse Vp contains an early portion of the post ventricular atrial blanking period PVAB where atrial sensing is blanked, an intermediate far field protection window FFPW where sensed atrial event is recorded but ignored, and a late PVARP window where any sensed atrial event is declared as atrial refractory sense event (Ars).

Figure 4:
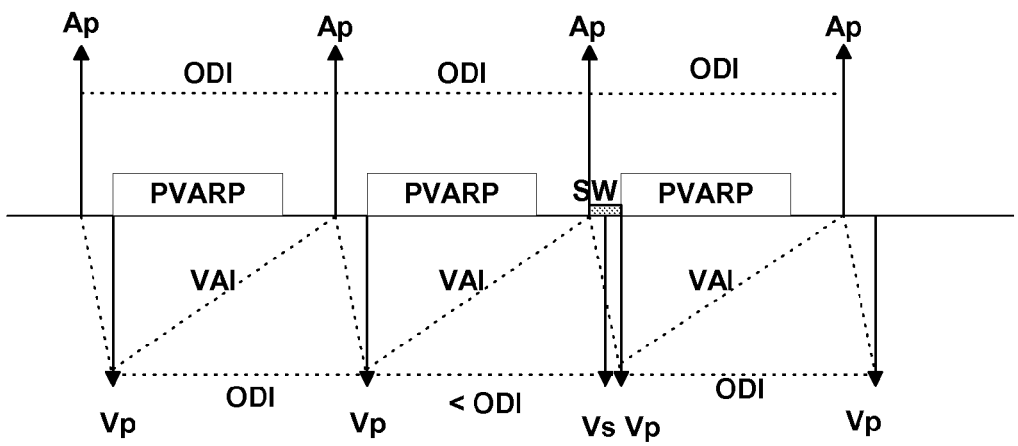
FIG. 4 is a diagram illustrating 3 cycles of DDI(R)+ where both atrium and ventricle are overdriven and there is an incidental SW Vs and SW Vp.

Refer to FIG. 4. Similarly, both atrium and ventricle are overdriven at a cycle length ODI with a short AVD. After the third atrial stimulation pulse Ap, there is a ventricular sense event Vs sensed during a safety window SW followed by a committed SW Vp. As a result, the interval from the second ventricular stimulation pulse Vp to the ventricular sense event Vs during the safety window SW is slightly less than ODI. After the SW Vp, the VV timer (with duration ODI) and VA timer (with duration ODI−AVD) start, and the atrium and ventricle are again overdriven with specified ODI.

Figure 5:
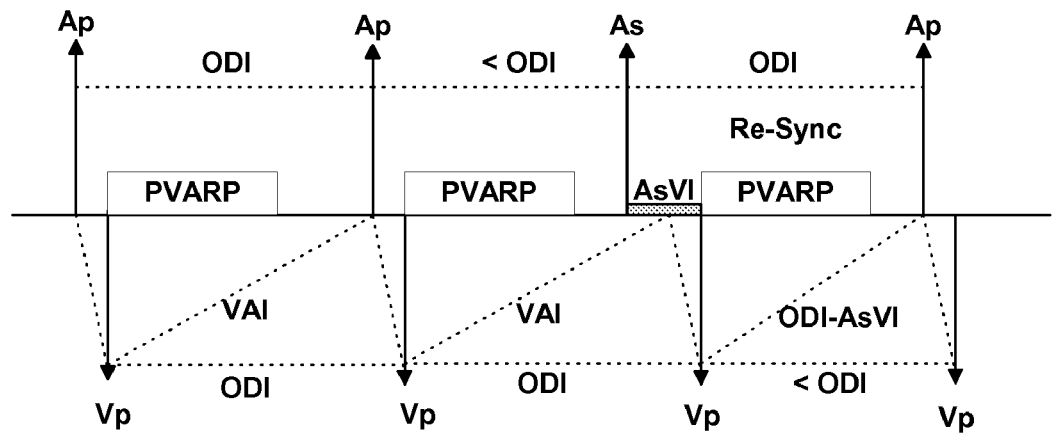
FIG. 5 is a diagram illustrating DDI(R)+ where both atrium and ventricle are overdriven and there is a used As that triggers the Re-Sync cycle.

Refer to FIG. 5. Again, both atrium and ventricle are overdriven at a cycle length ODI with a short AVD. After the second atrial stimulation pulse Ap, there is a used atrial sense event As (outside PVARP) that inhibits the scheduled atrial stimulation pulse Ap, and the Ap-As interval is shorter than ODI. This used As could be an atrial extrasystole AES, or an incidental atrial noise sense, or an intrinsic atrial depolarization due to subthreshold pacing of the second atrial stimulation pulse Ap, or an indication of transiently accelerated atrial rate such as due to enhanced heart rate variability or onset of proximal atrial tachycardia. Upon detection of the used atrial sense event As, a Re-Sync cycle is triggered, and the device starts to monitor the following ventricular event. Upon the detection of the following ventricular event, either Vs or Vp (a ventricular stimulation pulse Vp is shown in this example), the Re-Sync cycle is implemented. The implementation of the Re-Sync cycle is achieved by first measuring the interval between used atrial sense event As and the ventricular event V, AsVI. Then the VV timer and the VA timer are started with re-calculated intervals for this Re-Sync cycle. For the VV timer, the duration is calculated as: VVresync=max(ODI−AsVI+AVD, URL) with URL being an upper rate limit that is the shortest ventricular pacing interval at an upper stimulation rate limit. URL is not a rate but an interval although the name of this interval would indicate the opposite. For the VA timer, the duration is calculated as: VAresync=VVresync−AVD=max(ODI−AsVI, URL−AVD). As noted, the shortest ventricular pacing interval for the Re-Sync cycle is limited to URL. If there is no URL violation, then the closing atrial stimulation pulse Ap for the Re-Sync cycle will ensure the As-Ap interval equals ODI. By applying ODI coupled to the used As, the device can immediately regain control of the atrial overdrive. While the ventricular interval for the Re-Sync cycle is shorter than ODI, the closing ventricular stimulation pulse Vp for the Re-Sync cycle is coupled to the closing atrial stimulation pulse Ap, thus AV synchrony is maintained. After the Re-Sync cycle, the durations for the VV timer and VA timer are restored to their original values, so that both atrium and ventricle are continuously overdriven at the cycle length ODI. Also note that for fixed PVARP, because the used As is outside PVARP (i.e., AsVI<ODI−PVARP), the closing atrial stimulation pulse Ap also falls outside the PVARP (VAresync=ODI−AsVI>PVARP).

Figure 6:
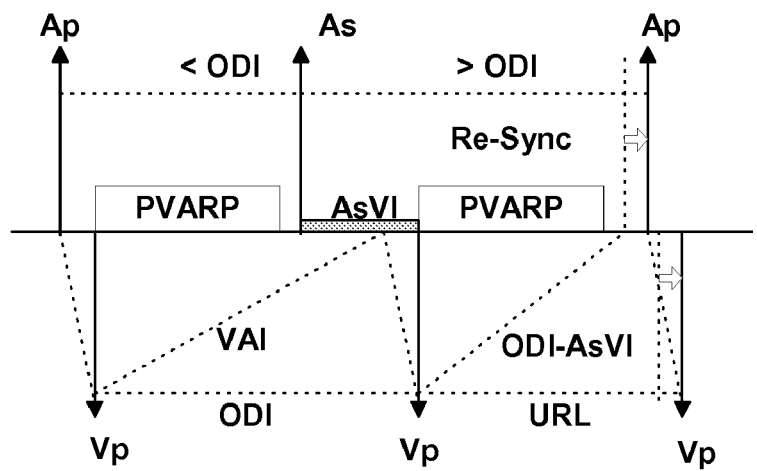
FIG. 6 is a diagram illustrating DDI(R)+ where both atrium and ventricle are overdriven and a used As triggers the Re-Sync cycle whose cycle length is limited by the URL.

Refer to FIG. 6. Similar to the example shown in FIG. 5, one used atrial sense event As triggers a Re-Sync cycle, and the following ventricular event V (Vp in this example) implements the Re-Sync cycle. However, in this example, it is found that (ODI−AsVI+AVD) is less than URL. Therefore, the duration of the VV timer is limited to URL, and the VA timer duration is set to (URL−AVD). As a result, the interval between the used As and the closing atrial stimulation pulse Ap for this Re-Sync cycle is longer than ODI.

Figure 7:
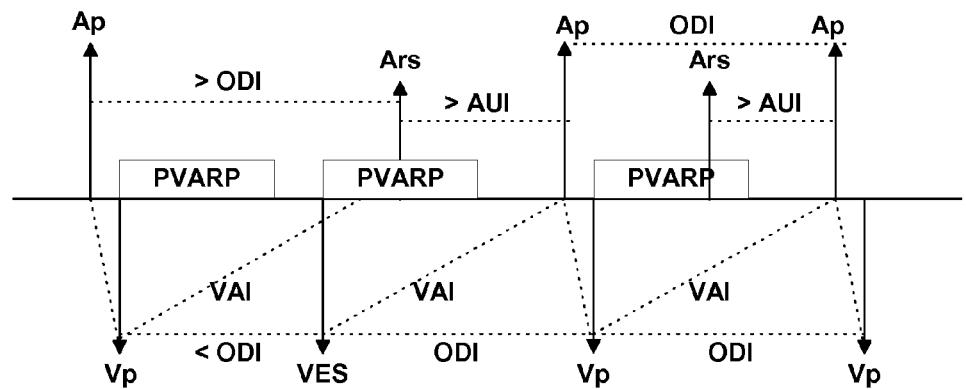
FIG. 7 is a diagram illustrating DDI(R)+ where both atrium and ventricle are overdriven and there is a VES and two Ars events without causing AUI violation.

Refers to FIG. 7. A ventricular extrasystole VES occurs while applying overdrive pacing to both atrium and ventricle. In a typical embodiment, the sensed ventricular event is declared as VES if it is not preceded by a used atrial event A (e.g., As outside PVARP or Ap). The VES starts a PVARP window that may have the same or different duration than the PVARP after a ventricular stimulation pulse Vp. The VES also resets the VV timer and VA timer, while the duration of each timer is unchanged. Also shown in this example are two refractory atrial sense events (Ars) that occur during the PVARP. The Ars could be a far-field sensing of the ventricular event, or a retrograde As due to ventricular stimulation pulse Vp or VES, or an atrial noise sense, or an intrinsic atrial depolarization due to sub-threshold pacing of the previous atrial stimulation pulse Ap. Upon detection of the Ars, the device calculates the interval from the Ars to the next scheduled atrial stimulation pulse Ap. As long as the calculated interval is longer than the programmed atrial upper interval (AUI, preferably 250 or 300 ms), there is no change on the VA timer duration or the VV timer duration.

Figure 8:
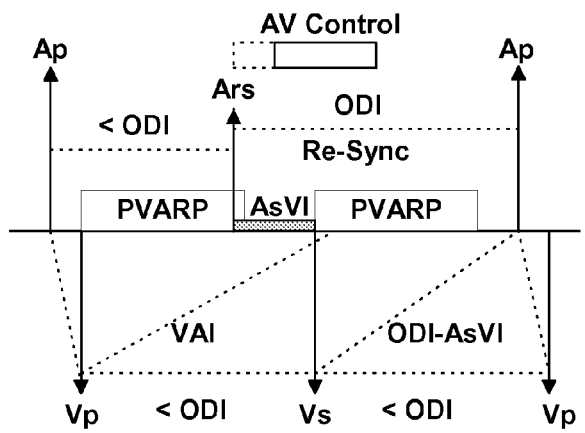
FIG. 8 is a diagram illustrating DDI(R)+ where both atrium and ventricle are overdriven and an Ars triggers the Re-Sync cycle and the conducted ventricular sense event Vs implements the Re-Sync cycle.

Refer to FIG. 8. In another embodiment, the sensed ventricular event can be declared as conducted ventricular sense event Vs if it is preceded by an Ars and the interval between Ars and Vs is within a predefined range, termed AV control time, preferably 150 ms-300 ms. This could happen if an AES occurs in the late PVARP and conducts to the ventricle as the example shown in FIG. 8. Accordingly, the Ars also triggers a Re-Sync Cycle, and the conducted ventricular sense event Vs implements the Re-Sync cycle. If there is no URL violation, then the closing atrial stimulation pulse Ap for the Re-Sync cycle will ensure the Ars-Ap interval equals ODI. By applying ODI coupled to the Ars, which is most likely an AES because of the following conducted ventricular sense event Vs, the device can immediately regain control of the atrial overdrive. On the other hand, if there is no detected ventricular sense event Vs within the AV control time, then the Re-Sync cycle is discarded.

Figure 9:
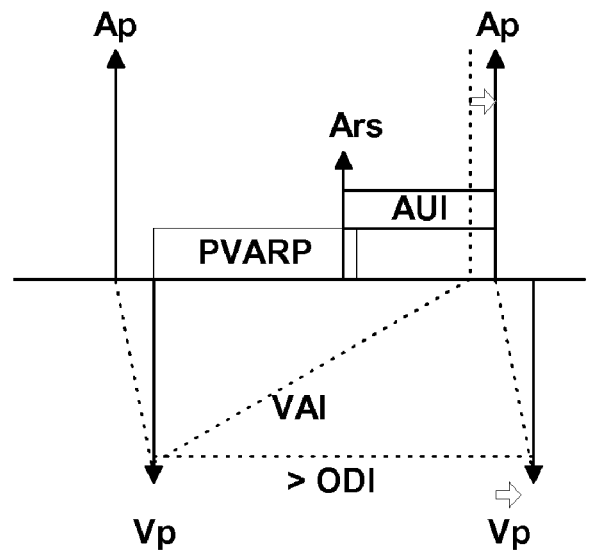
FIG. 9 is a diagram illustrating one cycle of DDI(R)+ where both atrium and ventricle are overdriven and one Ars causes rescheduling of the following Ap and Vp to avoid AUI violation.

Refer to FIG. 9. An Ars occurs while applying overdrive pacing to both atrium and ventricle. In this example, however, the interval from the Ars to the scheduled atrial stimulation pulse Ap is shorter than AUI. Upon detection of the AUI violation, the following atrial stimulation pulse Ap is delayed so that the Ars-Ap interval is equal to AUI. Correspondingly, the following ventricular stimulation pulse Vp is also rescheduled so that its interval to the Ars equals (AUI+AVD). The purpose of AUI is to prevent atrial stimulation pulse Ap being delivered during the atrial vulnerable period if the Ars is caused by an intrinsic atrial depolarization.

Figure 10:
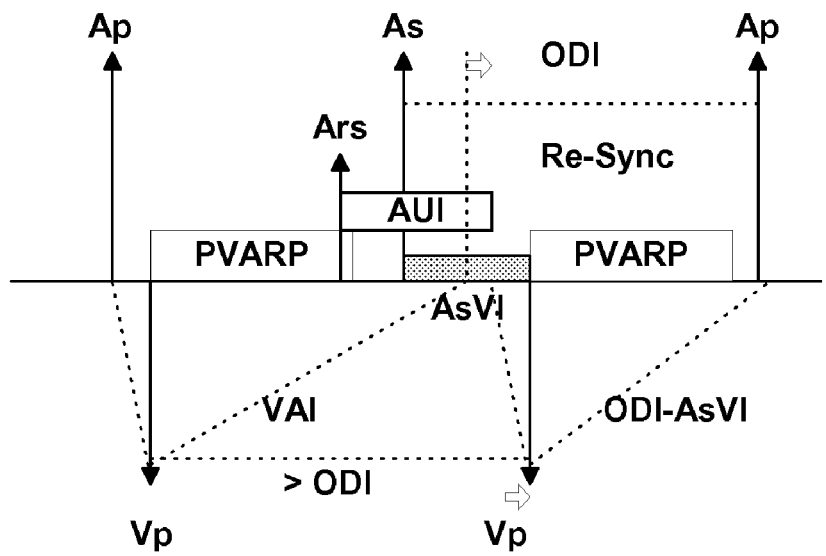
FIG. 10 is a diagram illustrating DDI(R)+ where both atrium and ventricle are overdriven and one Ars causes rescheduling of the following Ap and Vp to avoid AUI violation while another used As triggers a Re-Sync cycle.

Refer to FIG. 10. Similar to the example shown in FIG. 9, an Ars occurs while applying overdrive pacing to both atrium and ventricle and the following atrial stimulation pulse Ap and ventricular stimulation pulse Vp are postponed to avoid AUI violation. Because of the delayed atrial stimulation pulse Ap, there is a possibility for the occurrence of an intrinsic As that inhibits the rescheduled atrial stimulation pulse Ap (due to prolonged Ap-Ap interval), particularly if the Ars is not an intrinsic atrial event (e.g., due to noise sense or far-field sense). As in FIG. 5 and FIG. 6, this used As triggers a Re-Sync cycle, and the following ventricular event (Vp in this example) implements the Re-Sync cycle by recalculating the VV timer and the VA timer. Similarly, when atrial stimulation pulse Ap and ventricular stimulation pulse Vp are postponed in order to avoid URL violation (as the example shown in FIG. 6), there is also a possibility for the occurrence of an intrinsic As that inhibits the rescheduled atrial stimulation pulse Ap. As expected, such a used As will also trigger a Re-Sync cycle and the following ventricular event will implement the Re-Sync cycle in the same manner.

Figure 11:
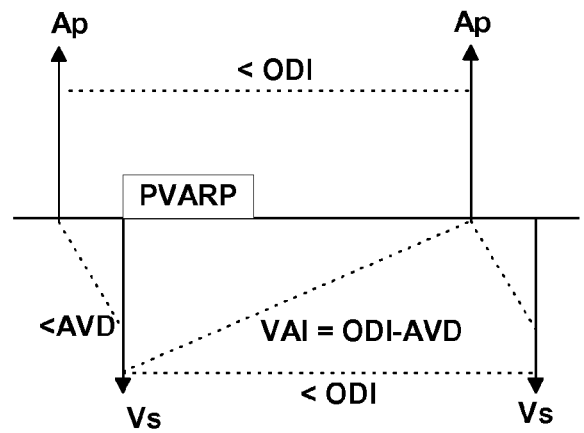
FIG. 11 is a diagram illustrating a typical cycle of DDI(R)+ where atrium is overdriven followed by conducted Vs.

Now refer to FIG. 11. In this example, a long AVD is programmed and the patient has intact AV conduction. As a result, the atrium is overdriven while each atrial stimulation pulse Ap is followed by a conducted ventricular sense event Vs. After each ventricular sense event Vs, a VV timer starts with duration of ODI, and a VA timer starts with duration of (ODI-AVD). However, because atrial stimulation pulse Ap is followed by conducted ventricular sense event Vs which inhibits the scheduled ventricular stimulation pulse Vp, the Ap-Vs interval is shorter than AVD. Consequently, the effective Ap-Ap interval and the measured Vs-Vs interval are slightly shorter than ODI (by a difference of AVD minus the Ap-Vs interval). As known in the art, the PVARP after ventricular sense event Vs is usually different than the PVARP after ventricular stimulation pulse Vp. In a typical embodiment, the PVARP after ventricular sense event Vs is also the FFPW where sensed atrial events are ignored.

Figure 12:
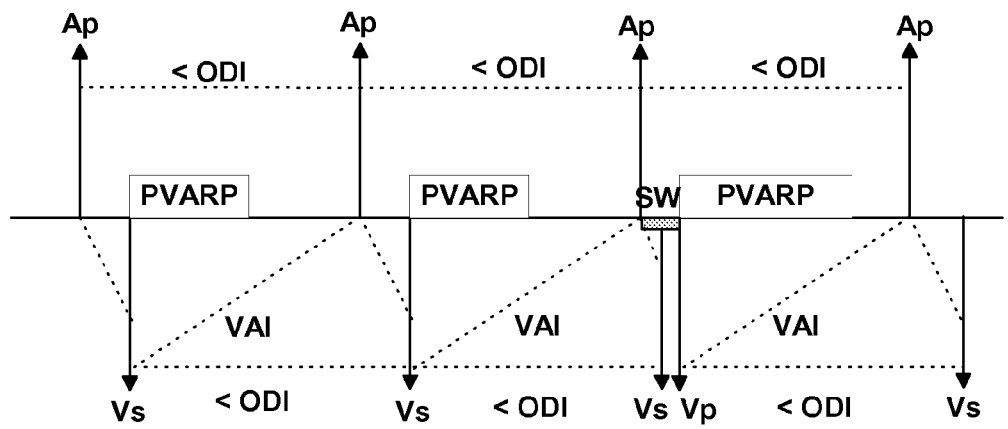
FIG. 12 is a diagram illustrating 3 cycles of DDI(R)+ where atrium is overdriven followed by conducted Vs and there is an incidental SW Vs and SW Vp.

Refer to FIG. 12. Similarly, conducted ventricular sense event Vs accompany atrial overdrive pacing. After the third atrial stimulation pulse Ap, there is a SW Vs which is followed by a committed SW Vp. After the SW Vp, the VV timer (with duration ODI) and the VA timer (with duration ODI-AVD) start. The atrium is continually overdriven with an effective pacing interval slightly shorter than ODI, and conducted ventricular sense event Vs follows the atrial stimulation pulse Ap. Note that in this example, the PVARP after ventricular sense event Vs is shorter than the PVARP after the SW Vp.

Figure 13:
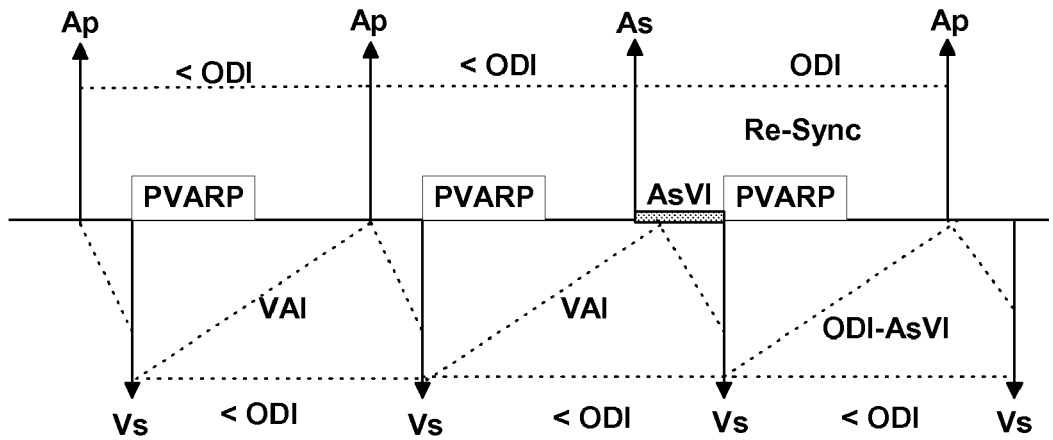
FIG. 13 is a diagram illustrating DDI(R)+ where conducted Vs accompany the atrial overdrive pacing and there is a used As that triggers the Re-Sync cycle.

Refer to FIG. 13. Again, conducted ventricular sense event Vs accompany atrial overdrive pacing. After the second atrial stimulation pulse Ap, there is a used As that inhibits the scheduled atrial stimulation pulse Ap. Similar to the case shown in FIG. 5, upon detection of the used As, a Re-Sync cycle is triggered, and the device starts to monitor the following ventricular event. Upon the detection of the following Vs or Vp (a ventricular sense event Vs is shown in this example), the Re-Sync cycle is implemented. The implementation of the Re-Sync cycle is the same as described above. That is, the interval between used As and the ventricular event, AsVI, is measured. The durations for the VV timer and the VA timer are re-calculated as: VVresync=max(ODI−AsVI+AVD, URL) and VAresync=VVresync−AVD=max(ODI−AsVI, URL−AVD). As noted, the shortest ventricular pacing interval for the Re-Sync cycle is limited to URL. If there is no URL violation, then the closing atrial stimulation pulse Ap for the Re-Sync cycle will ensure the As-Ap interval equals to ODI. By applying ODI coupled to the used As, the device can immediately regain control of the atrial overdrive. Similarly, the closing ventricular stimulation pulse Vp for the Re-Sync cycle is coupled to the closing atrial stimulation pulse Ap, thus the AV synchrony is maintained. After the Re-Sync cycle, the durations for the VV timer and VA timer are restored to their original values, so that atrium is continuously overdriven while conducted ventricular sense event Vs is allowed. Also note that for fixed PVARP, because the used As is outside PVARP (i.e., AsVI<ODI−PVARP), the closing atrial stimulation pulse Ap also falls outside the PVARP (VAresync=ODI−AsVI>PVARP).

Figure 14:
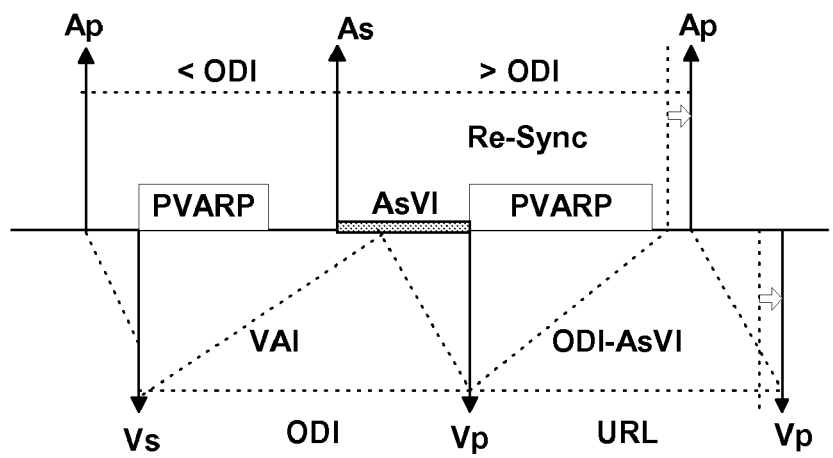
FIG. 14 is a diagram illustrating DDI(R)+ where conducted Vs accompany the atrial overdrive pacing and there is a used As that triggers the Re-Sync cycle whose cycle length is limited by the URL.

Refer to FIG. 14. Similar to the example shown in FIG. 13, one used As triggers a Re-Sync cycle, and the following ventricular event (Vp in this example) implements the Re-Sync cycle. However, in this example, it is found that (ODI−AsVI+AVD) is less than URL. Therefore, the duration of the VV timer is limited to URL, and the VA timer duration is set to (URL−AVD). As a result, the interval between the used As and the closing atrial stimulation pulse Ap for this Re-Sync cycle is longer than ODI.

Figure 15:
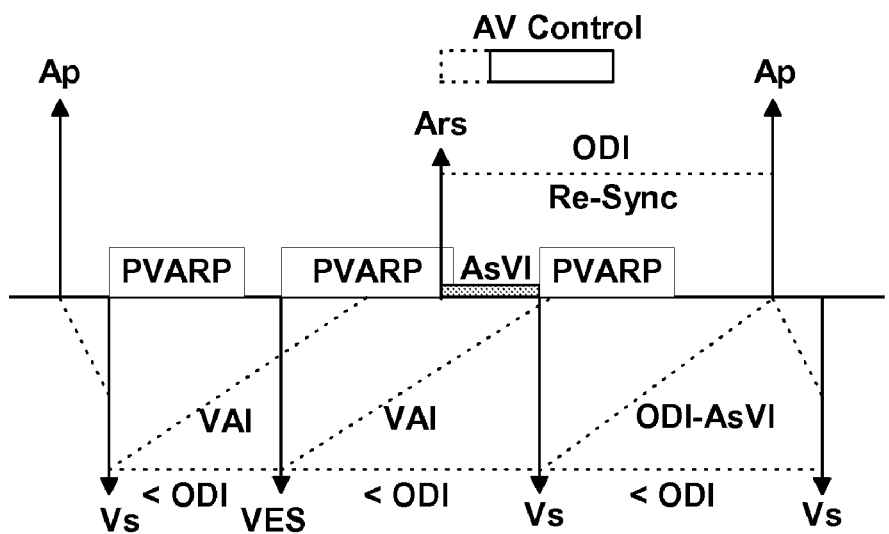
FIG. 15 is a diagram illustrating DDI(R)+ where conducted Vs accompany the atrial overdrive pacing and an Ars after VES triggers the Re-Sync cycle and the conducted Vs implements the Re-Sync cycle.

Refer to FIG. 15. In one embodiment, the sensed ventricular event is declared as conducted ventricular sense event Vs if it is preceded by an Ars and the interval between Ars and Vs is within a predefined range, termed AV control time, preferably 150 ms-300 ms. As the example shown in FIG. 15, this could happen if an intrinsic atrial event is detected during the PVARP after a VES, and the Ars is followed by a conducted ventricular sense event Vs (note in this example, the PVARP after VES is longer than the PVARP after Vs). Accordingly, the Ars triggers a Re-Sync Cycle, and the conducted ventricular sense event Vs implements the Re-Sync cycle. If there is no URL violation, then the closing atrial stimulation pulse Ap for the Re-Sync cycle will ensure the Ars-Ap interval equals ODI. By applying ODI coupled to the Ars, which is most likely an intrinsic As because of the following conducted ventricular sense event Vs, the device can immediately regain control of the atrial overdrive. On the other hand, if there is no detected ventricular sense event Vs within the AV control time, then the Re-Sync cycle is discarded. Yet in another embodiment, the sensed ventricular event can also be declared as VES if it is not preceded by a used atrial event (e.g., As outside PVARP or Ap). Similar to the example shown in FIG. 7, if a VES occurs, it simply resets the VV timer and VA timer, while the duration of each timer is unchanged.

Figure 16:
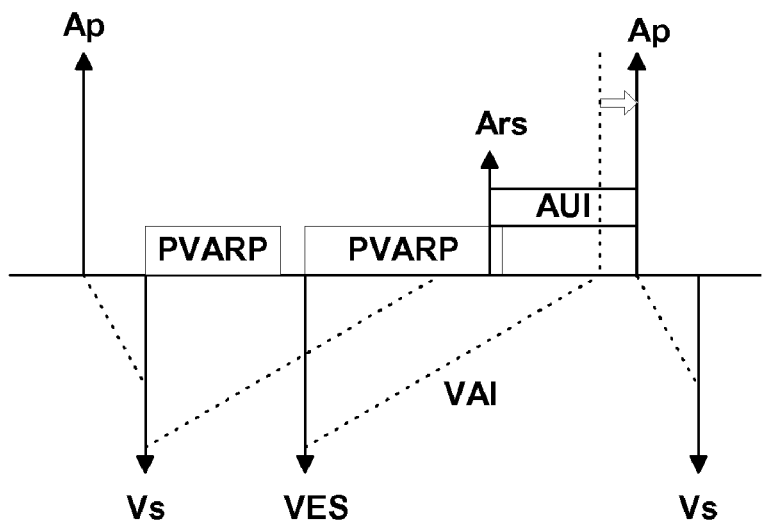
FIG. 16 is a diagram illustrating DDI(R)+ where conducted Vs accompany the atrial overdrive pacing and an Ars after VES that causes rescheduling of the following Ap and Vp to avoid AUI violation.

Refer to FIG. 16. Again, assume conducted ventricular sense event Vs accompany atrial overdrive pacing. In this example, an Ars occurs during the PVARP which is started by a VES, and the interval from this Ars to the next scheduled atrial stimulation pulse Ap is shorter than AUI. To avoid the AUI violation, the following atrial stimulation pulse Ap is delayed so that the Ars-Ap interval is equal to AUI. Correspondingly, the following ventricular stimulation pulse Vp is also rescheduled so that its interval to the Ars equals to (AUI+AVD). Note that in this example, the conducted ventricular sense event Vs following the rescheduled atrial stimulation pulse Ap inhibits the rescheduled ventricular stimulation pulse Vp. On the other hand, if the Ars did not cause AUI violation (i.e., the interval from the Ars to the following Ap is longer than AUI), then it would have no effect on the VA timer or the VV timer. As discussed before, whenever atrial stimulation pulse Ap and ventricular stimulation pulse Vp are postponed in order to avoid AUI violation or URL violation, there is a possibility for the occurrence of an intrinsic As that inhibits the rescheduled atrial stimulation pulse Ap. As expected, in such cases, the detected As will trigger a Re-Sync cycle, and the following ventricular event will implement the Re-Sync cycle.

Figure 17:
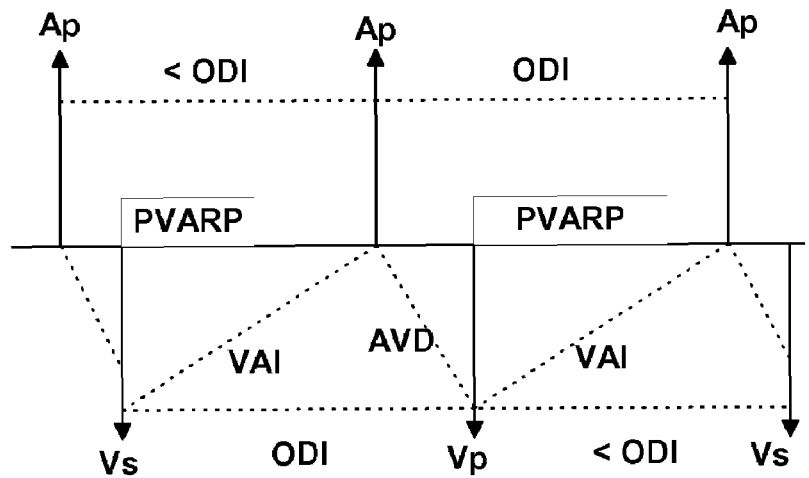
FIG. 17 is a diagram illustrating DDI(R)+ where both conducted Vs and Vp may accompany the atrial overdrive pacing.

Now refer to FIG. 17. In this example, the atrium is still overdriven. However, the AVD is comparable to the intrinsic AV conduction time, thus both Vs and Vp may follow the atrial stimulation pulse Ap. As shown in the figure, the first atrial stimulation pulse Ap and the third atrial stimulation pulse Ap are each followed by conducted ventricular sense event Vs while the second atrial stimulation pulse Ap is followed by a ventricular stimulation pulse Vp. As a result, the atrium is persistently overdriven at the effective cycle length of ODI (after Ap-Vp) or slightly shorter than ODI (after Ap-Vs), while ventricular event (Vp or Vs) is synchronized to each atrial stimulation pulse Ap. As described above, all the special handlings for SW Vs (trigger SW Vp and start VV and VA timers), VES (reset VV and VA timers), used As (trigger Re-Sync cycle limited by URL), Ars (check AUI violation and trigger Re-Sync cycle), etc., remain the same.

Another condition that should be considered is the loss of atrial overdrive for multiple cardiac cycles (evidenced by frequent As or Ars without Ap). This could happen in the case of unstable atrial rhythm or accelerating atrial rate (e.g., at the onset of the atrial tachyarrhythmia). As described above, Ars may postpone the following atrial stimulation pulse Ap and ventricular stimulation pulse Vp to avoid AUI violation, thus opening window for the occurrence of used As which will inhibit the scheduled atrial stimulation pulse Ap and trigger a Re-Sync cycle.

Figure 18:
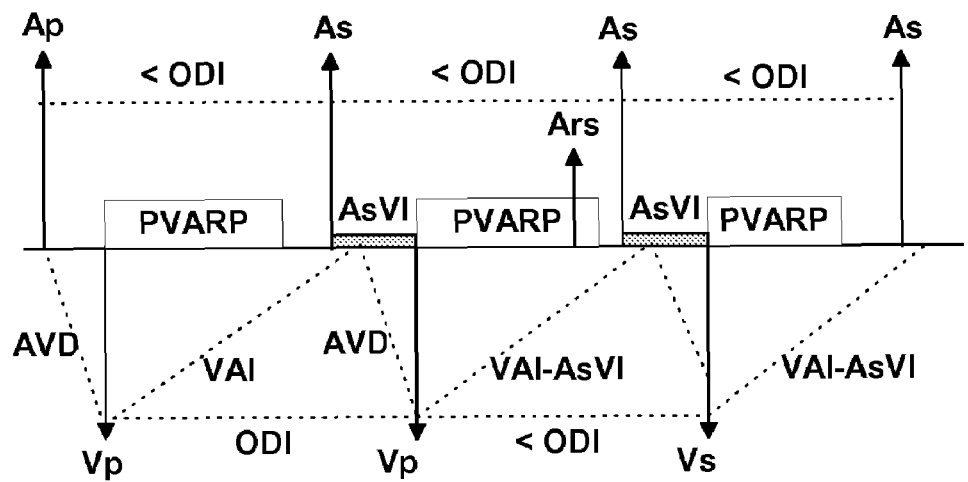
FIG. 18 is a diagram illustrating DDI(R)+ where atrial overdrive pacing is lost due to a transient increase of the atrial rate.

The Re-Sync cycle is re-triggerable. That is, before the delivery of the closing atrial stimulation pulse Ap of the Re-Sync cycle, if there is another Ars or As occurs, then the Re-Sync cycle is re-triggered. Upon the detection of the ventricular event after the Re-Sync cycle is triggered, the AsVI is always measured from the most recent As (latest trigger). Because the Re-Sync cycle is re-triggerable, in certain circumstances, it is possible that the Re-Sync cycle is repeatedly triggered while not a single one is completed by the closing atrial stimulation pulse Ap. In other words, the atrium loses the overdrive control. One example is illustrated in FIG. 18. In this example, the first cycle starts with an Ap-Vp pair. Before the delivery of the scheduled atrial stimulation pulse Ap, a used As is detected which triggers a Re-Sync cycle. Because no ventricular sense event Vs is detected after the As, the second ventricular stimulation pulse Vp is delivered at the end of the VV timer (duration ODI). Meanwhile, the device tries to implement the Re-Sync cycle based on the AsVI measured from the As to the second ventricular stimulation pulse Vp. However, before the delivery of the closing atrial stimulation pulse Ap for the Re-Sync cycle, an Ars and another used As are detected. Upon the detection of the Ars, the device checks against AUI violation and reschedules the atrial stimulation pulse Ap and ventricular stimulation pulse Vp if necessary. The Ars also triggers a new Re-Sync cycle. If there were no following As, then the device would either implement or discard the new Re-Sync cycle dependent on the presence or absence of a conducted ventricular sense event Vs within the predefined AV control time. However, in this example, there is another used As after the Ars. This used As re-triggers the Re-Sync cycle, and its interval to the following ventricular sense event Vs (AsVI) is used to implement the Re-Sync cycle. Again, before the delivery of the closing atrial stimulation pulse Ap for the new Re-Sync cycle, another As is detected which triggers a new Re-Sync cycle. As a result, none of the Re-Sync cycles is completed by the closing atrial stimulation pulse Ap, thus the control of atrial overdrive is lost.

When the loss of atrial overdrive is suspected, for example, consecutive number of Re-Sync cycles or frequent triggering of Re-Sync cycles (e.g., using X-out-of-Y criteria), then adjustment of the overdrive stimulation rate OSR and the overdrive interval ODI can be made in order to regain control of the atrial overdrive. Alternatively, the device may opt to exit the overdrive stimulation mode. As known in the art, the Mode Switch (MS) can be activated when the detected high atrial rate and the associated patterns meet the MS criteria.

In another condition, if VV timer and VA timer are repeatedly reset by the sensed ventricular events (e.g., frequent VES, non-sustained VT, etc.), then unstable ventricular rhythm or accelerated ventricular rate is suspected. The frequent reset of the VA timer may also cause the loss of atrial overdrive. In such circumstances, the device may opt to exit the overdrive mode. Alternatively, as known in the art, the device may detect the high ventricular rate and appropriate therapy may be applied.

What is claimed is:

1. A heart stimulator for stimulating at least an atrium and a ventricle of a heart, the heart stimulator comprising:
    electrode leads comprising electrodes configured
        to pick up electric potentials inside at least one atrium and at least one ventricle of a heart, and/or,
        to deliver electric stimulation pulses to said at least one atrium and said at least one ventricle of said heart;
    at least one sensing stage connected to said electrode leads, wherein said at least one sensing stage is configured to sense an excitation or a contraction of a heart chamber;
    at least one stimulation pulse generator configured to generate the electric stimulation pulses and connected to said electrode leads;
    a control unit, which is connected to said at least one sensing stage and to said at least one stimulation pulse generator and which is configured
        to trigger the electrical stimulation pulses that are generated by said at least one stimulation pulse generator and that are to be delivered via said electrode leads comprising said electrodes;
        to perform at least a mode of pacing
            wherein an atrial or a ventricular stimulation pulse is triggered in an atrium asynchronous manner when a respective atrial or ventricular escape interval times out because no intrinsic atrial or ventricular contraction is sensed during said respective atrial or ventricular escape interval, respectively;
            wherein a trigger of the atrial or a ventricular stimulation pulse is inhibited, when the intrinsic atrial or ventricular contraction, respectively, is sensed prior to time out of the respective atrial or ventricular escape interval;

and wherein the atrial and the ventricular escape interval corresponds to an overdrive stimulation rate, that is higher than an intrinsic heart rate; and, to resynchronize atrial stimulation and ventricular stimulation after an atrial sense event As or an atrial refractory sense event Ars is sensed during an atrial escape interval and is followed by a ventricular sense Vs or a ventricular pace Vp event, wherein said control unit is further configured to recalculate a ventricular escape interval and said atrial escape interval based on an AsV-Interval AsVI, which begins with said atrial sense event As or said atrial refractory sense event Ars and which ends with a following ventricular sense event Vs or ventricular pace event Vp so that an interval from the atrial sense event As or the atrial refractory sense event Ars to a next atrial stimulation pulse corresponds to the overdrive stimulation rate, and a next ventricular stimulation pulse is synchronized to a next atrial stimulation pulse such that the ventricular escape interval for resynchronization VVresync equals:

$$VVresync = \max(ODI - AsVI + AVD, URL)$$

wherein ODI is an overdrive interval that corresponds to the overdrive stimulation rate and wherein AVD is a predetermined atrioventricular delay interval and wherein URL is a shortest possible ventricular pacing interval that corresponds to a preset maximum stimulation rate and and said atrial escape interval for resynchronization VAresync equals:

$$VAresync = VVresync - AVD = \max(ODI - AsVI, URL - AVD).$$

2. The heart stimulator according to claim 1, wherein said control unit is configured to adjust said overdrive stimulation rate based on an intrinsic atrial rate sensed via said at least one sensing stage such that said overdrive stimulation rate is higher than said sensed intrinsic atrial rate prior to performing said mode of pacing with said overdrive stimulation rate.

3. The heart stimulator according to claim 1, wherein said control unit is configured to adjust said overdrive stimulation rate based on an activity signal determined by an activity sensor such that said overdrive stimulation rate is higher than an adapted heart rate that corresponds to a hemodynamic need that corresponds to an activity as determined by said activity sensor.

4. The heart stimulator according to claim 1, wherein said ventricular escape interval is a VV-interval started by a ventricular event.

5. The heart stimulator according to claim 1, wherein said atrial escape interval is a VA-interval started by a ventricular event.

6. The heart stimulator according to claim 5, wherein said atrial escape interval is a VA-interval that corresponds to VA=VV−AVD.

7. The heart stimulator according to claim 1, wherein said atrioventricular delay interval AVD is adjustable.

8. The heart stimulator according to claim 1, wherein said control unit is configured to apply only once the recalculated ventricular and atrial escape intervals after said atrial sense event As or atrial refractory sense event Ars is sensed which is followed by a ventricular event and to restore said ventricular and atrial escape intervals to their previous values if no further atrial event is sensed.

* * * * *